US00RE35352E

United States Patent [19]

Peters

[11] E Patent Number: Re. 35,352

[45] Reissued Date of Patent: Oct. 15, 1996

[54] METHOD FOR INTRALUMINALLY INDUCING CARDIOPLEGIC ARREST AND CATHETER FOR USE THEREIN

[75] Inventor: William S. Peters, Woodside, Calif.

[73] Assignee: Heartport, Inc., Redwood City, Calif.

[21] Appl. No.: 588,791

[22] Filed: Jan. 19, 1996

Related U.S. Patent Documents

Reissue of:

[64] Patent No.: 5,433,700
Issued: Jul. 18, 1995
Appl. No.: 159,815
Filed: Nov. 30, 1993

[30] Foreign Application Priority Data

Dec. 3, 1992 [AU] Australia ..... PL6170

[51] Int. Cl.[6] ..... A61M 37/00

[52] U.S. Cl. ..... 604/4; 604/28; 604/96; 604/113

[58] Field of Search ..... 604/4, 5, 28, 49, 604/51–53, 96–103, 113; 606/21, 192, 194; 600/18; 128/898

[56] References Cited

U.S. PATENT DOCUMENTS

| | | |
|---|---|---|
| 3,769,960 | 11/1973 | Robinson . |
| 4,173,981 | 11/1979 | Mortensen et al. . |
| 4,276,874 | 7/1981 | Wolvek et al. . |
| 4,527,549 | 7/1985 | Gabbay . |
| 4,531,936 | 7/1985 | Gordon . |
| 4,540,399 | 9/1985 | Litzie et al. . |
| 4,592,340 | 6/1986 | Boyles . |
| 4,601,713 | 7/1986 | Fuqua . |
| 4,664,125 | 5/1987 | Pinto . |
| 4,697,574 | 10/1987 | Karcher et al. . |
| 4,705,507 | 11/1987 | Boyles . |
| 4,741,328 | 5/1988 | Gabbay . |
| 4,785,795 | 11/1988 | Singh . |
| 4,804,365 | 2/1989 | Litzie et al. . |
| 4,877,035 | 10/1989 | Bogen et al. . |
| 4,889,137 | 12/1989 | Kolobow . |
| 4,902,272 | 2/1990 | Milder et al. . |
| 4,902,273 | 2/1990 | Choy et al. . |
| 4,943,275 | 6/1990 | Stricker . |
| 5,011,469 | 4/1991 | Buckberg et al. . |
| 5,116,305 | 5/1992 | Milder et al. . |
| 5,167,628 | 12/1992 | Boyles . |
| 5,176,619 | 1/1993 | Segalowitz . |
| 5,176,628 | 1/1993 | Boyles . |
| 5,186,713 | 2/1993 | Raible . |
| 5,195,942 | 3/1993 | Weil et al. . |
| 5,219,326 | 6/1993 | Hattler . |
| 5,254,097 | 10/1993 | Schock et al. . |
| 5,308,320 | 5/1994 | Safar . |
| 5,312,344 | 5/1994 | Grinfeld et al. . |

FOREIGN PATENT DOCUMENTS

| | | |
|---|---|---|
| 218275 | 4/1987 | European Pat. Off. . |
| 92/17118 | 10/1992 | WIPO . |

OTHER PUBLICATIONS

Partington, M. T. "Studies of retrograde cardioplegia: II. Advantages of antegrade/retrograde cardioplegia to optimize distribution in jeopardized myocardium", J. Thorac Cardiovasc Surgery, 1989, 97(4):613–622.

(List continued on next page.)

*Primary Examiner*—John D. Yasko
*Attorney, Agent, or Firm*—Townsend and Townsend and Crew LLP

[57] ABSTRACT

A process for inducing cardioplegic arrest of a heart in situ in a patient's body, comprising maintaining the patient's systemic circulation by peripheral cardiopulmonary by-pass, occluding the ascending aorta through a percutaneously placed arterial balloon catheter, venting the left side of the heart, and introducing a cardioplegic agent into the coronary circulation. This procedure readies the heart for a variety of surgical procedures that can be performed percutaneously through lumina in the catheter. An aortic catheter for use in the process is also described.

17 Claims, 6 Drawing Sheets

OTHER PUBLICATIONS

Textbook of Surgery, 10th ed. (W. B. Saunders Company, Philadelphia, 1972) pp. 2021–2023, 2114–2121.
Ishizaka, M. "Myocardial protection by retrograde cardiac perfusion with cold modified krebs solution through coronary sinus during complete ischemic arrest for 120.", Ass. Thorac Surg (Japan), 25(12):1592–1601 (1977).
Takahashi, M. "Retrograde coronary sinus perfusion for mycardial protection in aortic valve surgery", Jpn Assoc Thorac Surg. 30(3):306–318 (1982).
Gundry et al. "A comparison of retrograde cardiolegia versus antegrad cardioplegia in the presence of coronary artery obstruction" Ann Thorac Surg, 38(2):124–127 (1984).
Lust et al. "Improvedprotection of chronically inflow–limited myocardium with retrograde coronary sinus cardioplegia", Circulation 78(5pt2)III217–223 (1988).
Crooke et al. "Biventricular Distribution of Cold Blood Cardioplegic Solution Administered by different retrograde techniques", J. Thorac Cardiovasc Surg. 10240:631–636 (1991).
Razi, "The challege of cacific aortitis", J. Card Surg 8:102–107 (1993).
Ogawa et al. "Aortic arch reconstruction without aortic cross–clamping using separate extra corporeal circulation", J. Jpn Assoc Thorac Surg, 41(11):2185–2190 (1993).
Buckberg, G. D. "Strategies and ogic of Cardioplegic Delivery to Prevent, Avoid, and Reverse Ischemic and Reperfusion Damage", J. Thorac Cardio Vasc Surg, 93:127–129 (1987).
Yamaguchi, A. "A Case of a Reoperation Using a Balloon Catheter with Blocked Pars Ascendes Aortae", Kyobu Geka, 42(11):961–964 (1991).
Rossi, F. "Long–Term Cardiopulmonary Bypass by Peripheral Cannulation in a Model of Total Heart Failure", J. Thorac Cardio Vasc Surg, 100:914–921 (1990).
Sabiston, D. C. Textbook of Surgery, 10th Ed, 2021–2023, 2114–2121, (1972).
Uchida et al. "Percutaneous Cardiomyotomy and Valvulotomy with Angioscopic Guidance", American Heart J 121(4, Pt 1):1221–1224 (1991).
Uchida et al., "Percutaneous Fiberoptic Angioscopy of the Cardiac Valves", American Heart J, 121(6, part 1):1791–98 (1991).
"Occlusion Balloon Catheters: Instructions for Use", Medi–Tech, Boston Scientific Corporation, Rev. Mar. 1991.
Cosgrove, D. M. "Management of the Calcified Aorta: An Alternative Method of Occlusion" Ann Thorac Surg. 36:718–719 (1983).
Foster and Threlkel "Proximal Control of Aorta with a Balloon Catheter" Surg. Gynecology & Obstetrics, pp. 693–694 (1971).
Erah, Jr. and Stoney, Jr. "Balloon Catheter Occlusion of the Ascending Aorta" Ann Thorac Surg. 35:560–561 (1983).

METHOD FOR INTRALUMINALLY INDUCING CARDIOPLEGIC ARREST AND CATHETER FOR USE THEREIN

Matter enclosed in heavy brackets [ ] appears in the original patent but forms no part of this reissue specification; matter printed in italics indicates the additions made by reissue.

*This application is a reissue of Ser. No. 08/159,815 filed Nov 30, 1993 now U.S. Pat. No. 5,443,700.*

FIELD OF THE INVENTION

The present invention relates to a method for inducing cardioplegic arrest in a heart and to catheters for use in that method.

1. Background Art

The use of extracorporeal cardiopulmonary by-pass for cardiac support has become well established. This use has, however, involved median sternotomy or less commonly thoracotomy with all of the trauma that necessarily accompanies such a major surgical procedure.

The present invention contemplates, at least in its preferred embodiments, the possibility of effective ascending aortic occlusion, cardioplegia, venting, right heart deflation and topical cooling-in association with extracorporeal cardiopulmonary by-pass all without necessitating a median sternotomy or other thoracic incision.

2. Disclosure of the Invention

In a first aspect the present invention consists in a method for inducing cardioplegic arrest of a heart in situ in a patient's body, comprising the steps of:

(a) maintaining systemic circulation with peripheral cardiopulmonary by-pass;

(b) occluding the ascending aorta through a percutaneously placed arterial balloon catheter;, (c) introducing a cardioplegie agent into the coronary circulation; and (d) venting the left side of the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous by-pass system to be associated with cardioplegia, venting and cooling of the heart which subverts the need for median sternotomy. This may, in turn, reduce the complications of the surgery.

The maintenance of the systemic circulation involves establishing a cardiopulmonary by-pass. The blood may be drawn into the by-pass merely by positioning a percutaneous catheter into the right atrium and/or into one or both of the vena cavae through which venous blood may be drawn from the heart into an extracorporeal pump oxygenator. In more preferred embodiments of the invention a single catheter with two inflatable cuffs, or two separate catheters, each with an inflatable cuff are introduced into the vena cavae to occlude them adjacent to their right atrial inlets. This allows isolation of the fight atrium and allows blood to be drawn from the vena cavae into the by-pass system. There is also preferably provision for percutaneous communication via one catheter with the right atrium to allow infusion of saline into the right atrium. This infusion has the advantage that it allows the heart to be cooled and improves visual acuity within the right heart allowing direct cardioscopic examination and/or intervention.

The catheter used to decompress the right atrium and to draw blood into the by-pass is preferably introduced through the femoral vein by percutaneous puncture or direct cut down. If other than simple venous drainage is required catheters with inflatable cuffs, as described above, are placed preferably such that an inflatable cuff of the cannula is positioned within each of the inferior (suprahepatic) and superior vena cavae. There is preferably a lumen in the cannula acting as a common blood outlet from the vena cavae leading to the pump oxygenator. A separate lumen is preferably used to infuse saline between the two inflated cuffs into the right atrium. If, alternatively, separate catheters are used to occlude each of the inferior and superior vena cavae then the cannula for the inferior vena cavae is preferably introduced percutaneously from the femoral vein and that for the superior vena cavae is introduced percutaneously through the jugular or subclavian vein.

The ascending aorta is preferably occluded by a balloon catheter introduced percutaneously through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon is of a cylindrical shape to fully and evenly accommodate the lumen of the ascending aorta. This maximises, the surface area contact with the aorta, and allows for even distribution of occlusive pressure.

The balloon of the catheter is preferably inflated with a saline solution to avoid the possibility of introducing into the patient an air embolism in the event that the balloon is ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg has been proven effective in trials.

The aortic catheter is preferably introduced under fluoroscopic guidance over a suitable guidewire. Transoesophageal echocardiography can alternatively be used for positioning as has been described with reference to the venous catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml/min of caxdioplegic solution can be introduced into the aortic root under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fibre-optic light camera of no greater than 3 mm diameter. It is however, preferable that the diameter and cross-sectional design of the internal lumina is such that the external diameter of the catheter in its entirety is small enough to allow its introduction into the adult femoral artery by either percutaneous puncture or direct cut-down.

The oxygenated blood returning to the body from the by-pass system may be conveyed into the aorta from another lumen in the cannula carrying the balloon. In this case the returning blood is preferably discharged from the catheter in the external iliac artery. In another embodiment of the invention, and in order to reduce the diameter of the catheter carring the balloon, a separate arterial catheter of known type may be used to return blood to the patient from the by-pass system. In this case a short catheter is positioned in the other femoral artery to provide systemic arterial blood from the bypass system. The control end of the catheter, i.e. that end that remains outside of the body, should have separate ports of attachment for the lumina. The catheter length should be approximately 900 mm for use in humans.

The cardioplegic agent may be any of the known materials previously known to be useful, or in the future found to be useful, as cardioplegic agents. The agent is preferably infused as a solution into the aortic root through one of the lumina of the aortic catheter.

In another aspect the present invention consists in a catheter for use in occluding the ascending aorta comprising an elongate tube having one or more continuous lumina along its length, an inflatable cuff is disposed about the tube adjacent one end thereof, the cuff being of such a size that upon being inflated it is able to occlude the ascending aorta of a patient.

The catheter and method according to the present invention can be used to induce cardioplegic arrest and may be used in a number of surgical procedures. These include the following:

1. Coronary artery revascularisation such as:

(a) angioscopic laser introduction or angioscopic balloon angioplasty catheter into the coronary arteries via one lumen of the aortic catheter, or (b) thoraco dissection of one or both of the mammary arteries with revascularisation achieved by distal anastomoses of the internal mammary arteries to coronary arteries via a small left anterior thoracotomy.

2 Secundum-type arterial septal defect repair such as by:

(a) "Closed" cardioscopic closure, or (b) Closure as an "open" procedure via a mini-right thoracotomy.

3. Sinus venosus defect repairs similar to 2 above.

4. Infundibular stenosis relief by cardioscopie techniques.

5. Pulmonary valvular stenosis relief by cardioscopic techniques.

6. Mitral valve surgery via a small right thoracotomy.

7. Aortic stenosis relief by the introduction of instrumentation via a lumen in the aortic catheter into the aortic root.

8. Left ventricular aneurysm repair via a small left anterior thoracotomy.

BRIEF DESCRIPTION OF THE DRAWINGS

Hereinafter given by way of example are preferred embodiments of the present invention described with reference to the accompanying drawings in which.

BEST MODE OF CARRYING OUT THE INVENTION

Figure 1:
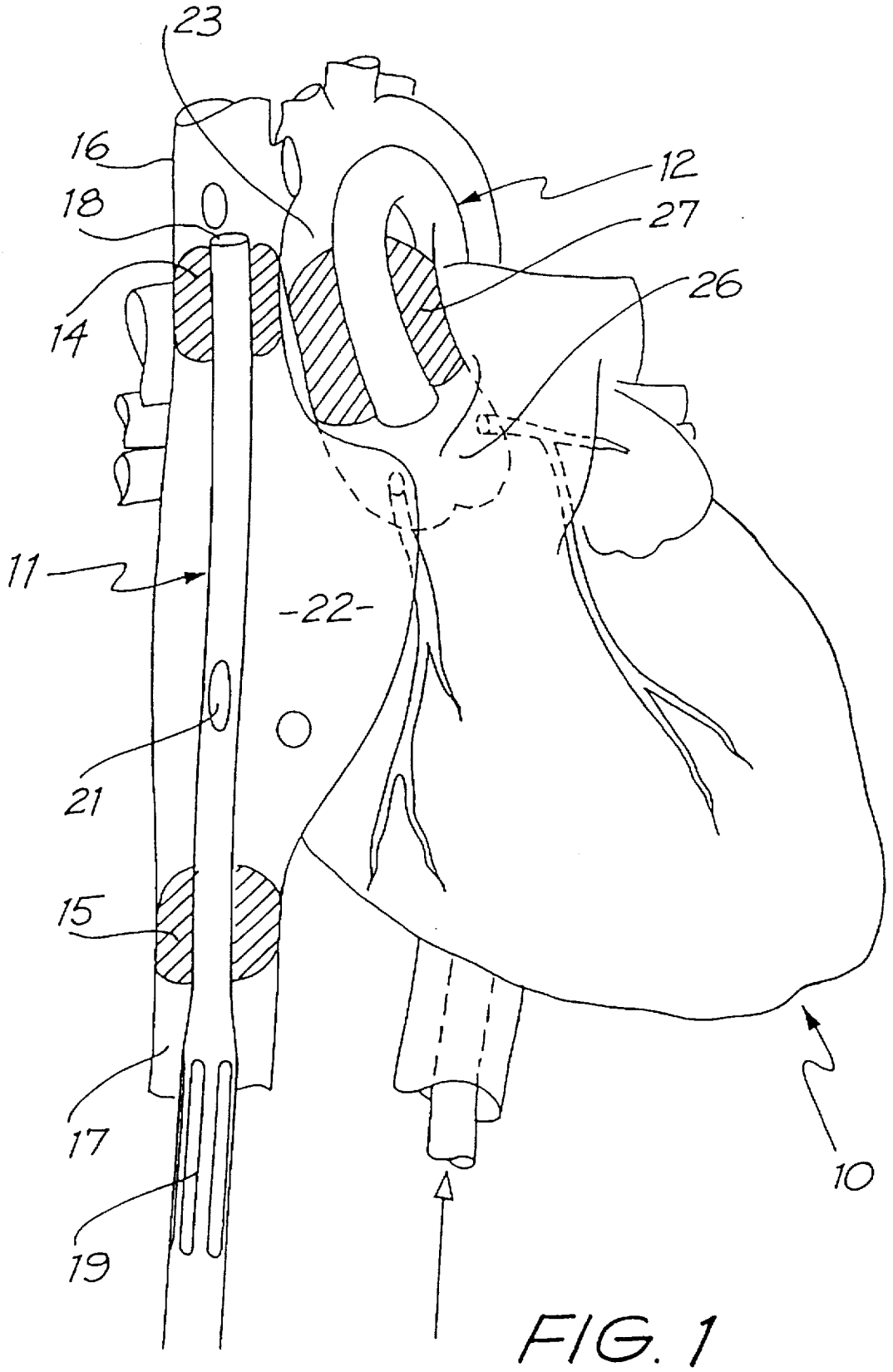
FIG. 1 is a schematic partly cut-away representation of a patients heart having percutaneous catheters placed therein for carrying out the method according to the present invention.
Figure 2:
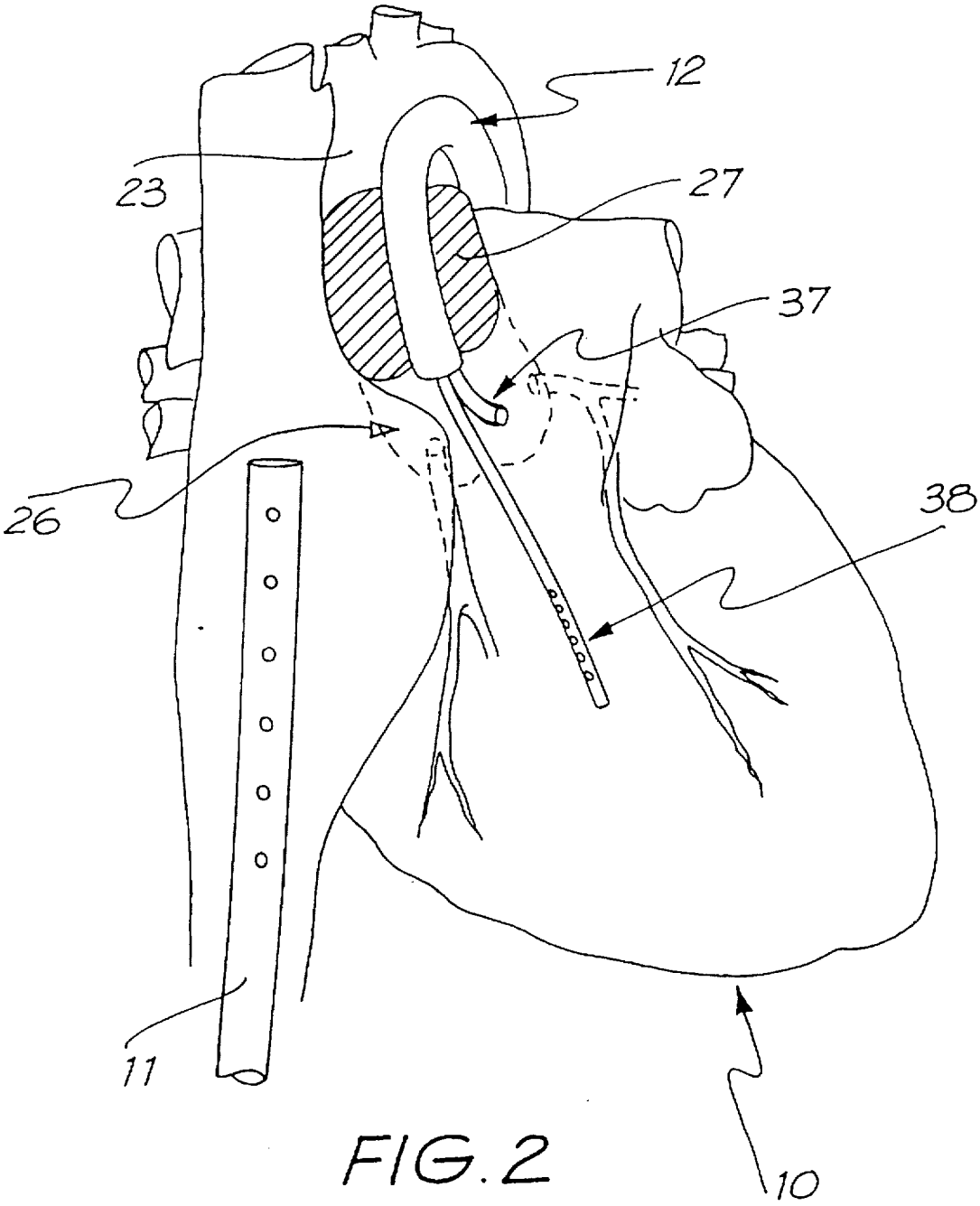
FIG. 2 is a similar view to FIG. 1 showing the aortic catheter in position but including an angioscope and a left ventricular venting cannula introduced into the aortic root and left ventricle respectively, via separate lumina within the aortic catheter.

The heart 10 of FIGS. 1 and 2 is positioned in the living body of a patient and is accessed percutaneously.

In order to induce cardioplegia in the heart while maintaining the patient it is necessary to divert the patients blood circulation through an extracorporeal cardiopulmonary by-pass system. This is achieved by isolating the heart 10 on both the venous and arterial sides using appropriate percutaneously inserted venous catheter 11, aortic balloon catheter 12, and if this catheter 12 doesn't have provision for arterial blood return, arterial catheter 39 (see FIG. 3). The venous outflow and arterial inflow lumina of the catheters 11 and 12 of the by-pass system are of sufficient cross sectional area to achieve standard blood flows to maintain the patient's systemic circulation during the period of extracorporeal circulation.

In the case of the use of a single venous double-ballooned catheter 11, as is shown in FIG. 1, the catheter 11 is inserted through the fernoral vein preferably. A suitable guide wire is initially inserted and the catheter 11 is then introduced in known manner under fluoroscopic guidance. The catheter 11 includes a pair of separately inflatable balloons 14 and 15 each connected to a balloon inflation control device (not shown) through suitable lumina in the catheter 11. The balloon 14 is adapted to occlude the superior vena cavae 16 while the balloon 15 is adapted to occlude the suprahepatic inferior vena cavae I7. A blood withdrawal lumen in the catheter 11 has an inlet orifice 18 flush with the balloon 14, to avoid venous collapse during blood flow into the catheter 11, and a series of inlet slots 19 in the inferior vena cavae. Blood drawn into the inlets 18 and 19 enter a common single lumen. Blood drawn into the by-pass system through the catheter 11 is oxygenated and returned to the patient in a manner which will be hereinafter described.

A separate lumen in the catheter 11 opens into the right atrium 22 through aperture 21 to allow evacuation of blood from the right heart and the infusion of saline to induce topical cooling and/or to improve visual acuity within the right heart.

Figure 9B:
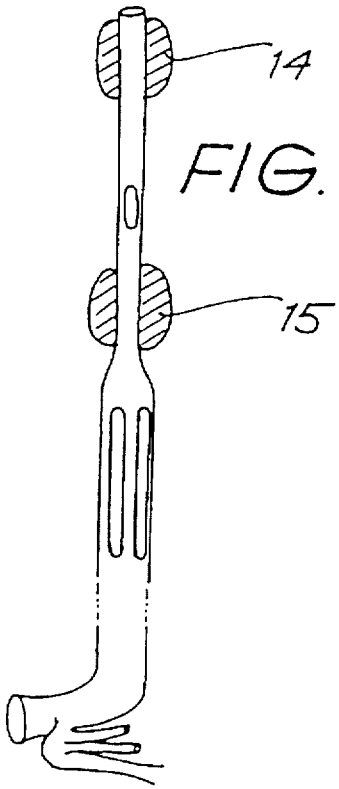
FIGS. 9a and 9b show schematically two alternative catheter arrangements for the isolation of the right atrium and venous drainage.
Figure 9A:
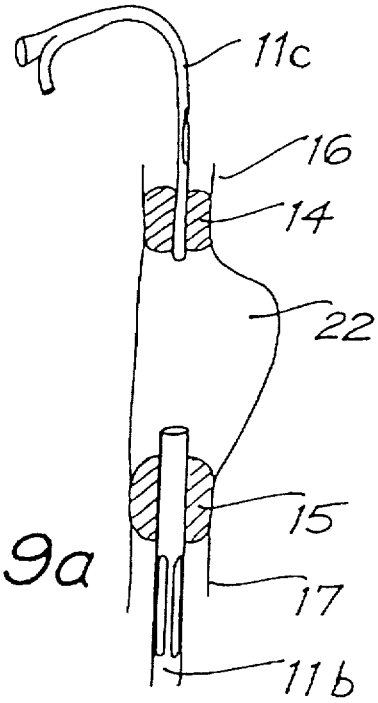

In use, after the catheter 11 has been positioned the balloons may be inflated or deflated to vary the rate of venous return to the right atrium 22 and therefore the degree of decompression of the left heart. Venous drainage may be effected by gravitational drainage or by applying a degree of negative pressure to assist flow into the pump oxygenator. It will be appreciated that the distance between the balloons 14 and 15 will need to be correct for a given patient and this may be assessed by X-ray examination to allow selection of an appropriately sized catheter. Alternatively separate catheters 11b and 11c could be used, as is shown in FIG. 9a, for the inferior and superior vena cavae. The cannula 11b being introduced as has been described above and the cannula 11c being introduced through the jugular or subclavian vein. It will also be appreciated that for simple operations not requiring complete occlusion of the right atrium it is possible to merely insert a simple catheter 11 into the right atrium to draw blood into the by-pass system as is seen in FIG. 2. Positioning under fluoroscopic guidance is not essential in this case.

Figure 3:
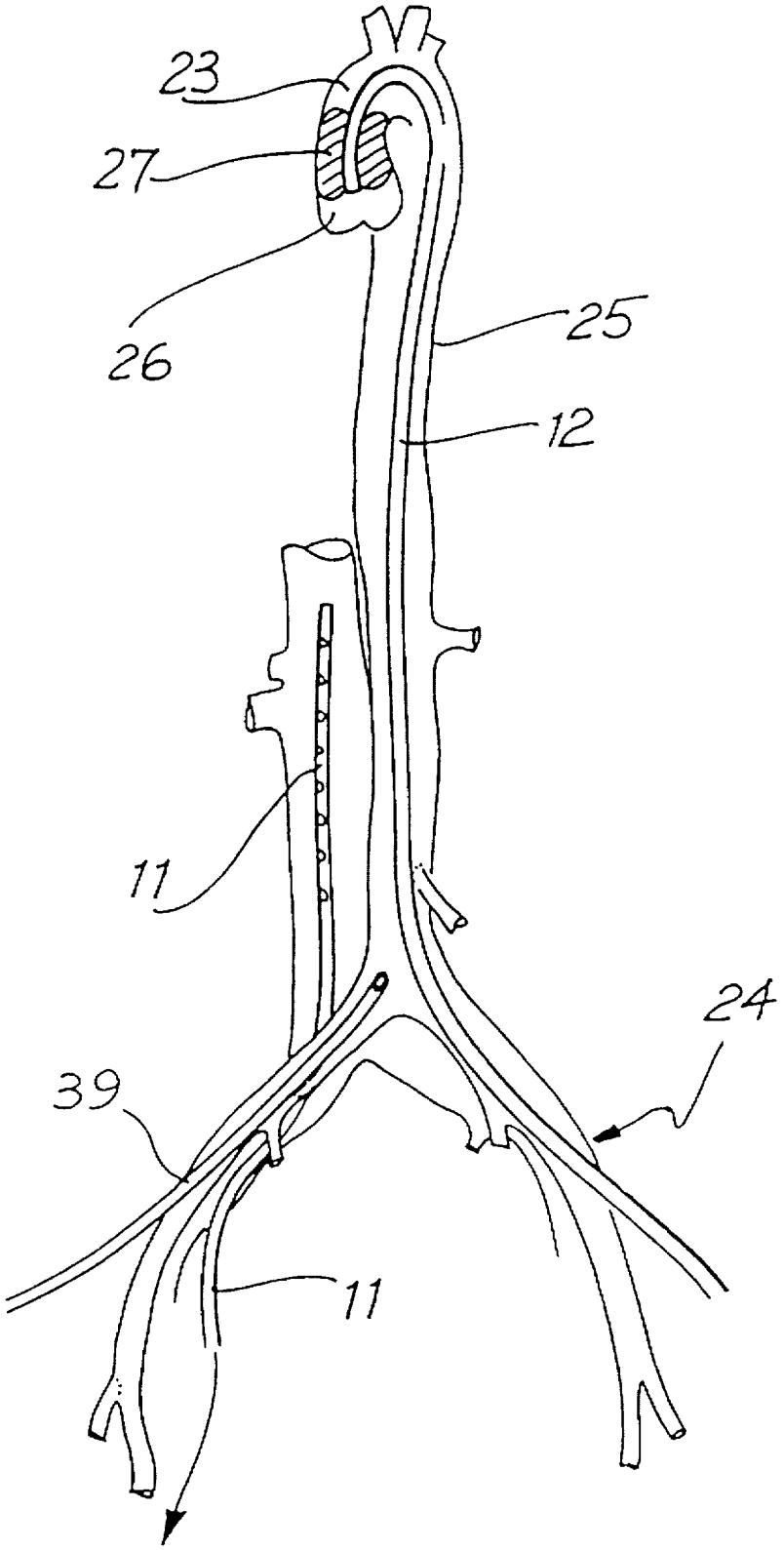
FIG. 3 is a front elevational view of part of the vascular system of a patient showing, inter alia, the aortic balloon catheter positioned in the ascending aorta via the femoral artery.

The catheter 12 is positioned in the manner described above with its free end located in the ascending aorta 23. The catheter 12 is so positioned by insertion preferably through the femoral artery 24 and via the descending aorta 25 as is seen in FIG. 3.

If desired a fluoroscopic dye may be introduced into the aortic root 26 through the catheter 12 for accurate positioning of the tip of the catheter 12 relative to the aortic root 26 and the coronary ostia.

The catheter 12 carries at its free end a balloon 27. The balloon 27 is arranged to be inflated with saline from an inflation control device 23 of known type through a lumen in the catheter 12. The device 28 is fired with a pressure gauge 29 to allow the operator to control the inflation of the balloon 27. The pressure of the fully inflated balloon 27 should be of the order of 350 mmHg so as to be sufficient to effectively occlude the aorta and to prevent the balloon moving while not being so great as to cause damage to the aortic wall. The balloon 27 should have a maximum diameter sufficient to occlude the aorta and for this purpose the maximum diameter should be about 35 mm. The balloon 27 should have a length of about 40 mm so as not to be so long as to occlude or impede blood flow to the coronary arteries on to the brachiocephalic, subclavian or carotid arteries. If necessary in any given patient the required length and diameter of the balloon may be determined by angiographic, X-ray examination or echocardiography and an appropriately sized catheter selected on that basis.

Figure 5:
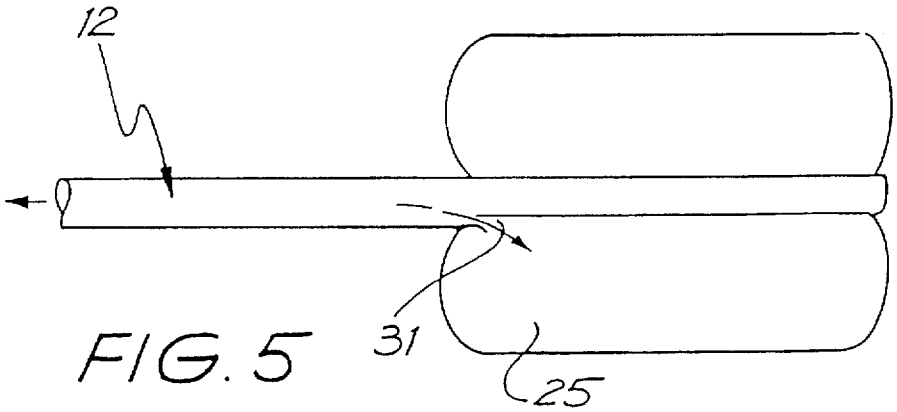
FIG. 5 is a partly cut away side elevational view of the balloon end of the catheter of FIG. 4 in an inflated condition.

The balloon 27 is preferably connected to the lumen 32 through which it is inflated at the end of the balloon 27 distal to the tip of the catheter 12 through orifice 31 (see FIG. 5). This allows the tip of the catheter to contain fewer lumina than the remainder of the catheter. Accommodation of the deflated balloon around the tip of the catheter is thus possible without adding to the diameter of the tip as compared with the rest of the catheter 12.

Figure 6A:
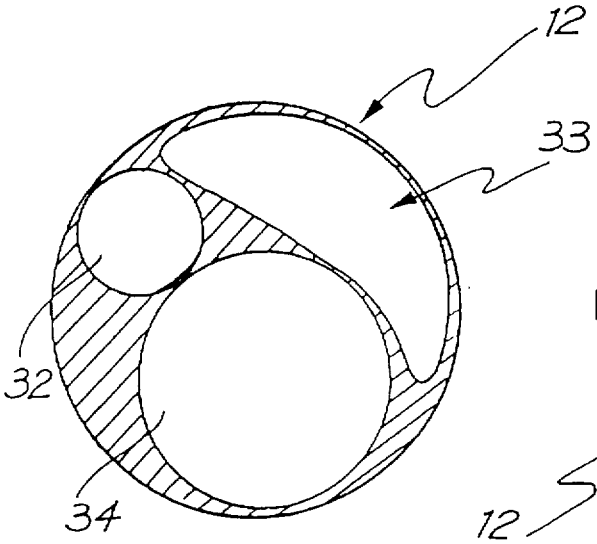
FIG. 6a is a cross-sectional view of the catheter of FIG. 4 intermediate the control end and the balloon end.
Figure 7:
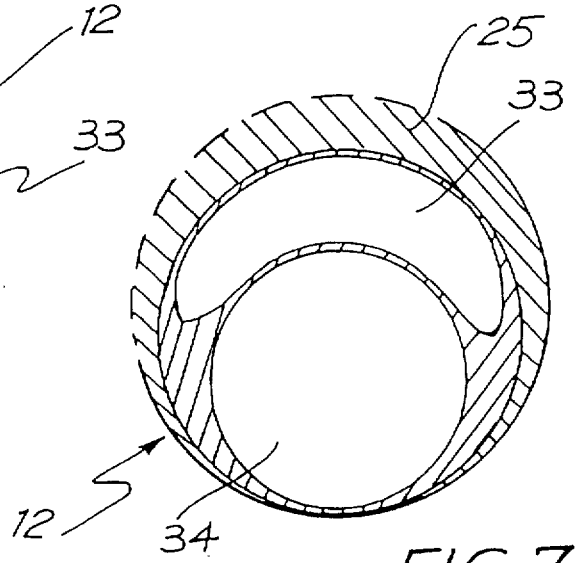
FIG. 7 is a cross-sectional view through the balloon end of the catheter of FIG. 4.
Figure 6B:
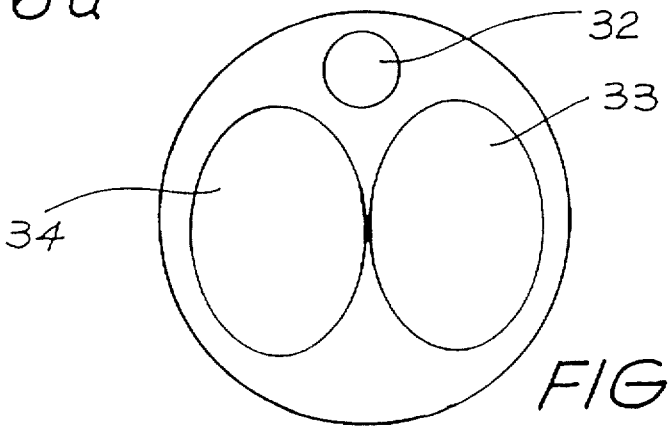
FIG. 6b is an alternative cross-sectional arrangement of the lumina in the catheter of FIG. 4.
Figure 8A:
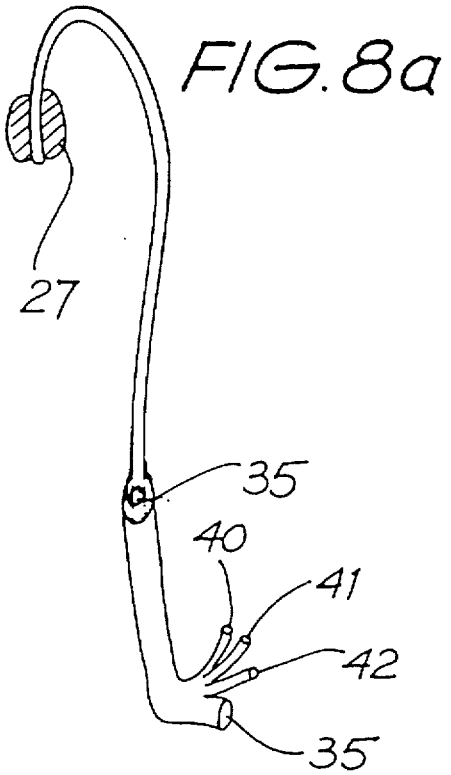
FIGS. 8a and 8b show schematically two alternative arrangements to the catheter shown in FIG. 4.
Figure 8B:
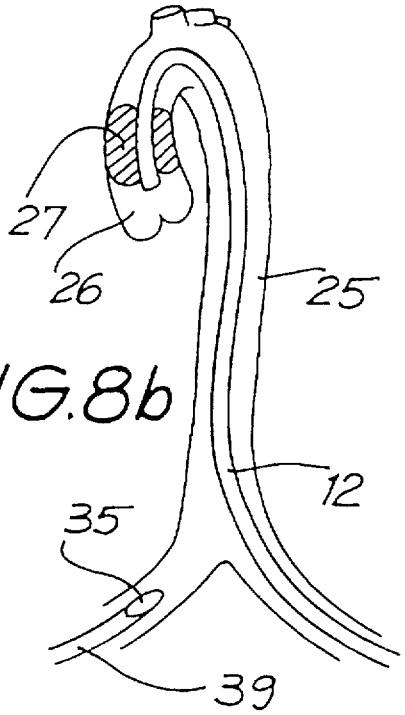

The catheter 12 includes a plurality of lumina (see FIGS. 6 and 7). In addition to the balloon inflation lumen 32 there is at least a single venting/cardioplegia lumen 33 of circular cross-section. There may be a separate and extra circular lumen 34 for instrumentation. If two lumens are present the venting/cardioplegia lumen may be circular or crescent shaped in cross-section (FIG. 6a, 6b). The diameter of the various lumina should be as small as practicable commensurate with the intended use. In addition there may be a continuous lumen 35 through which arterial blood is returned from the by-pass. This may flow out of the catheter 11 through an orifice in the region of the external iliac artery. In alternative embodiments of the invention such as shown in FIGS. 3 and 8 the arterial return lumen 35 may comprise its own catheter 39 of known type introduced into the other femoral artery or some other suitable artery.

Figure 4:
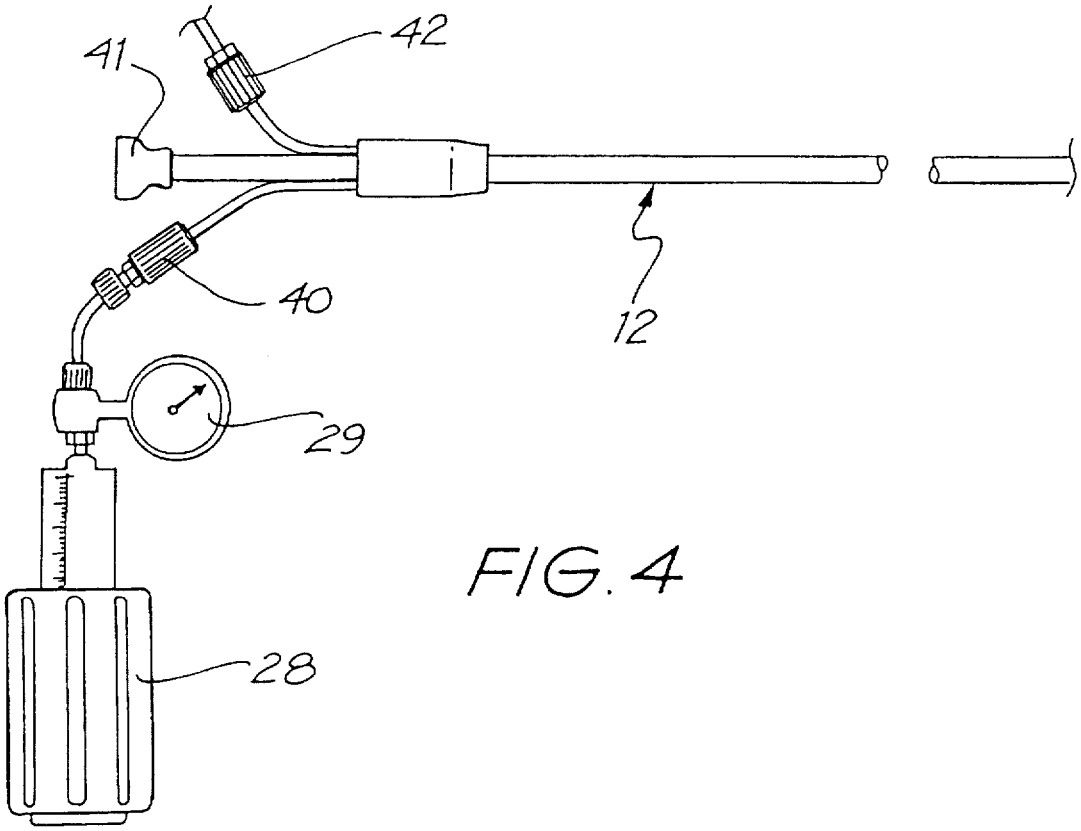
FIG. 4 is a side elevational view of the control end of the aortic catheter according to the present invention.

The control end of the catheter 12, illustrated in FIG. 4, has a plurality of ports of attachment 40, 41, 42 for each of the lumina 32, 33, 34, respectively. Inflation control device 18 and pressure gauge 19 may be connected to port 40 to allow the operator to control inflation of balloon 27.

In use the catheter 11 is introduced percutaneously by puncture or cutdown as has been described and once blood flow through the by-pass is established (including systemic cooling) flows are reduced and the balloon 27 is inflated. Flows are then returned to the operating levels and a suitable cardioplegic agent is introduced into the aortic root. Once the full volume of cardioplegic agent has been given and cardiac arrest achieved, the lumen is then used to vent the heart. The heart may then be operated on or examined by insertion of instrumentation 37 such as a cardioscope or a laser into the heart through the lumen 34 or through atrial trocars. Alternatively, with the heart on by-pass as described above the heart can be approached by an open method by an incision other than median sternotomy. Venting of the left ventricle may be effected by providing an extended cannula 38 projecting from lumen 33 into the left ventricle (see FIG. 2) or by simply applying negative pressure to the venting lumen 33 of the aortic catheter. To reverse cardioplegic arrest the body is rewarmed and the balloon 17 deflated. Aortic blood is thus allowed to perfuse the heart. Whilst the body remaim supported by peripheral cardiopulmonary bypass, the return of the heart rhythm is awaited. External defibrillation may be necessary. Weaning from by-pass is then completed in a routine fashion.

I claim:

1. A method for inducing cardioplegic arrest of a heart in situ in a patient's body, comprising the steps of:

(a) maintaining systemic circulation with peripheral cardiopulmonary by-pass;

(b) occluding at least one of the patient's vena cavae with an inflatable cuff on a distal portion of at least one percutaneously placed venous catheter to isolate a fight atrium of the heart from at least a portion of the patient's venous system;

(c) occluding the ascending aorta through a percutaneously placed arterial balloon catheter;

(d) introducing a cardioplegic agent into the coronary circulation; and (e) venting the heart through a percutaneously placed catheter.

2. A method as claimed in claim 1 in which the ascending aorta is occluded by an arterial balloon catheter percutaneously placed through one of the femoral arteries.

3. A method as claimed in claim 2 wherein the cardioplegic agent is introduced through a lumen in the arterial balloon catheter.

4. A method as claimed in claim 1 further comprising introducing a fluid into the right atrium through a lumen in a percutaneous venous catheter which opens between the two cuffs.

5. A method as claimed in claim 1 in which the percutaneous venous catheter is introduced into the heart through a femoral vein.

6. A method as claimed in claim 1 in which the systemic circulation is maintained through a cardiopulmonary by-pass that includes an oxygenated blood return catheter introduced into one of the femoral arteries.

7. A method as claimed in claim 1 wherein the vena cavae arc occluded with two inflatable cuffs, each inflatable cuff being on a separate percutaneously placed venous catheter.

8. A method as claimed in claim 1 wherein the vena cavae are occluded with two inflatable cuffs both disposed on a single percutaneously placed venous catheter.

9. A method as claimed in claim 1 further comprising withdrawing venous blood from at least one vena cava through a lumen in at least one of the percutaneously placed venous catheters and directing the venous blood to the cardiopulmonary by-pass.

10. A method as claimed in claim 4 wherein the fluid comprises saline.

11. A method as claimed in claim 1 wherein oxygenated blood is returned from the cardiopulmonary bypass to the patient's arterial system through a lumen in the arterial balloon catheter.

12. A method as claimed in claim 1 wherein the heart is vented by withdrawing fluid through a lumen in the arterial balloon catheter.

13. A method as claimed in claim 1 further comprising introducing an instrument through a lumen in the arterial balloon catheter into the patient's heart.

14. A method as claimed in claim 13 wherein the instrument comprises a scope, the method further comprising visualizing the heart with the scope.

15. A method as claimed in claim 13 wherein the instrument comprises a cannula having a lumen, the method further comprising venting fluids from the heart through the lumen in the cannula.

16. A method for inducing cardioplegic arrest of a heart in situ in a patient's body, comprising the steps of:

(a) positioning a percutaneously placed venous catheter in at least a portion of both of the patient's vena cavae and in a right atrium of the heart;

(b) occluding a superior vena cavae with a first inflatable cuff on a distal portion of the percutaneously placed venous catheter and occluding an inferior vena cavae with a second inflatable cuff on a distal portion of the percutaneously placed venous catheter to isolate the heart from at least a portion of the patient's venous system;

(c) withdrawing blood from the venous system through a lumen in the venous catheter;

(d) oxygenating the blood withdrawn from the venous system;

(e) returning the oxygenated blood to the patient's arterial system;

(f) occluding the ascending aorta through a percutaneously placed arterial balloon catheter, (g) introducing a cardioplegic agent into the coronary circulation; and (h) venting the heart through a percutaneously placed catheter.

17. A method for inducing cardioplegic arrest of a heart in situ in a patient's body, comprising the steps of:

(a) maintaining systemic circulation with peripheral cardiopulmonary bypass;

(b) isolating a fight atrium of the patient's heart from the patient's venous system with at least one perculta-neously placed venous catheter;

(c) isolating a coronary vasculature from the patient's arterial system with a percutaneously placed arterial balloon catheter;, (d) introducing a cardioplegic agent into the coronary vasculature; and (e) venting fluid from the heart through a percutaneously placed catheter.

* * * * *